United States Patent
Bell et al.

(10) Patent No.: US 8,389,752 B2
(45) Date of Patent: Mar. 5, 2013

(54) PREPARATION OF ALICYCLIC DIEPOXIDES

(75) Inventors: Andrew Bell, Lakewood, OH (US); Dane Jablonski, Brunswick, OH (US); Elaine Koronich, Novelty, OH (US); Yumiko Yamanoi, Tokyo (JP); Yoshiaki Fukunishi, Tokyo (JP); Kazunobu Senoo, Tokyo (JP)

(73) Assignee: Peomerus LLC, Brecksville, OH (US)

( * ) Notice: Subject to any disclaimer, the term of this patent is extended or adjusted under 35 U.S.C. 154(b) by 501 days.

(21) Appl. No.: 12/577,845

(22) Filed: Oct. 13, 2009

(65) Prior Publication Data

US 2010/0094030 A1    Apr. 15, 2010

Related U.S. Application Data

(60) Provisional application No. 61/104,317, filed on Oct. 10, 2008.

(51) Int. Cl.
   *C07D 301/03*    (2006.01)
   *C07D 303/00*    (2006.01)
(52) U.S. Cl. .......................... 549/547; 549/523
(58) Field of Classification Search .............. 549/544, 549/523, 547
   See application file for complete search history.

(56) References Cited

U.S. PATENT DOCUMENTS 3,183,249 A * 5/1965 Wiese ..................... 549/545

FOREIGN PATENT DOCUMENTS

| EP | 1 541 567 A1 | 6/2005 |
| EP | 2 039 692 A1 | 3/2009 |
| JP | 2004-099467 | 4/2004 |
| JP | 2004-204228 | 7/2004 |

OTHER PUBLICATIONS

Neftekhimiya, 1972, 12, pp. 353-357.
Diels-Alder reaction between butadiene and cyclopentadiene. Determination of trimers by Tsuchida, Shoichi; Hamanaka, Sewako; Ogawa, Masaya. Fac. Eng., Kansai Univ., Suita, Japan, Sekiyu Gakkaish (1972), 15(3), pp. 189-192. (English-Language Abstract).
Alder et al., Zur Kenntnis der Dien-Synthese, IV. Mitteil: Über den Aufbau von Diphenyl- und Fluoren-Ringsystemen; arylierte Äthylene als Olefinkomponenten für Dien-Synthesen, Chemische Berichte, Verlang Chermie, GmbH, Weinheim, DE, vol. 71, No. 2, Jan. 1, 1938, pp. 379-386.

* cited by examiner

*Primary Examiner* — Taylor Victor Oh
(74) *Attorney, Agent, or Firm* — The Webb Law Firm

(57) ABSTRACT

Embodiments in accordance with the present invention provide alicyclic diepoxide compounds and methods for forming such compounds. Such methods encompass charging a reaction vessel with an appropriate diene and an appropriate dienophile and causing such to react to form and recover a desired alicyclic diepoxide precursor where such precursor is subsequently epoxidized. Such compounds encompass alicyclic diepoxides having purities of at least 95 percent or at least 98 percent with respect non-isomeric residues and are essentially free of any isomeric alicyclic diepoxide residues.

7 Claims, 1 Drawing Sheet

GC-MS
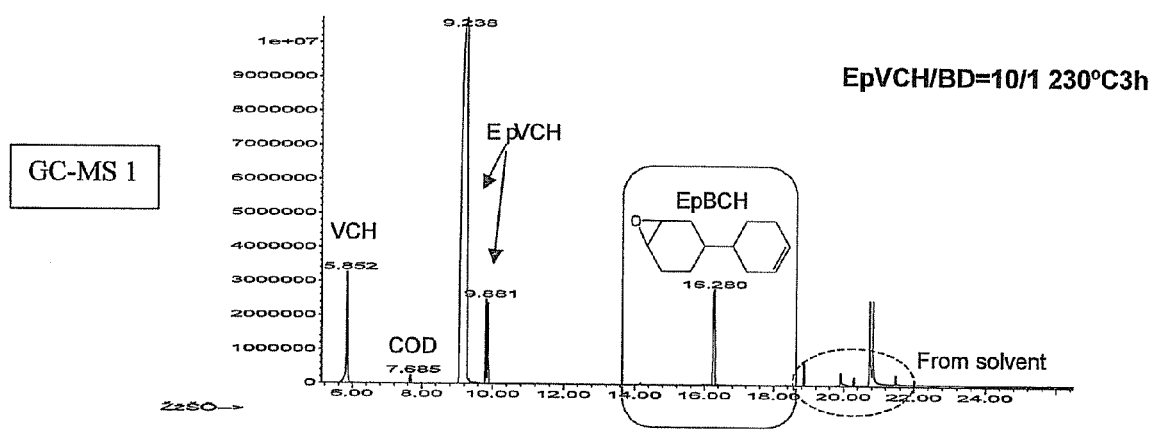
GC-MS 1
EpVCH/BD=10/1 230°C 3h
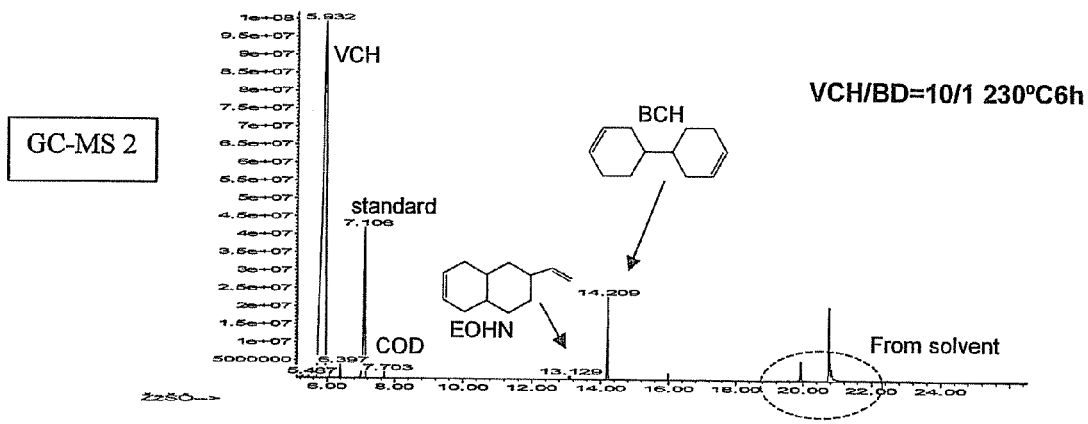
GC-MS 2
VCH/BD=10/1 230°C 6h

PREPARATION OF ALICYCLIC DIEPOXIDES

CROSS-REFERENCE TO RELATED PATENT APPLICATION

The present patent application is entitled to and claims the benefit of priority, under 35 U.S.C. §119 of U.S. Provisional Patent Application Ser. No. 61/104,317 filed Oct. 10, 2008, which is incorporated herein by reference in its entirety.

TECHNICAL FIELD

The present invention relates generally to the preparation of alicyclic epoxides and more specifically to the preparation high purity alicyclic diepoxides.

BACKGROUND

EP2039692A1, to Daicel Chemical Industries, LTD of Osaka, Japan, reports (see paragraph [0002]) that 3,4-epoxy-cyclohexylmethyl-3',4'-epoxycyclohexanecarboxylate, 1,2, 8,9-diepoxylimonene and a compound corresponding to a ∈-caprolactone oligomer, except with 3,4-epoxycyclohexyl-methanol and 3,4-epoxycyclohexanecarboxylic acid bonded to both terminals respectively through ester bonding (all being available from Daicel Chemical Industries, Ltd. under the trade names CEL-2021P, CEL-3000 and CEL-2081, respectively) give cured articles through reactions in the presence of various curing agents or curing catalysts where the properties of the resulting epoxy cured articles, thermal stability, transparency, and satisfactory dielectric properties, originate from the alicyclic skeletons of such compounds. However, in paragraph [0003] of the application, problems relating to the deterioration of properties in some applications or low reactivity for curing is noted for such exemplary materials.

At paragraph [0004], EP2039692A1 refers to three references for preparing a 3,4,3',4'-diepoxybicyclohexyl compound, JP-A No. 2004-99467, JP-A No. 2004-204228 and the Russian document Neftekhimiya, 1972, 12, 353, that each suffer from both insufficient reactivity upon curing and insufficient thermal stability of the cured article prepared therefrom. At paragraph [0007], the application disclosing that after intensive investigations, it was found that each of the aforementioned methods for preparing the 3,4,3',4'-diepoxy-bicyclohexyl compound suffered from also providing "not small amounts of isomers differing typically in the position of epoxy groups on the cyclohexane ring". Further, such paragraph reports that by an alternate process discovered by the inventors they use could the 3,4,3',4'-diepoxybicyclohexyl compound having a very small content of isomers and that curing of such compound provided "a cured article that has a higher glass transition temperature to thereby have significantly improved properties such as thermal stability" with "a very high curing reaction rate".

As a result, at paragraph [0008] EP2039692A1 states that "in the present invention, an alicyclic diepoxy compound comprises a 3,4,3',4'-diepoxybicyclohexyl compound represented by following Formula (1):

[Chemical Formula 1]

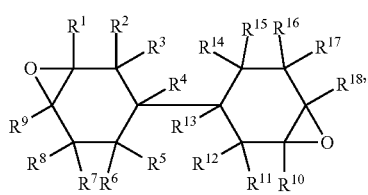

(1)

where "In the Formula (1), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are the same as or different from one another and each represent a hydrogen atom, a halogen atom, a hydrocarbon group which may have an oxygen atom or a halogen atom, or a substituted or unsubstituted alkoxy group. The alicyclic diepoxy compound may contain an isomer of the 3,4,3',4'-diepoxybicyclo-hexyl compound as an impurity. When the isomer is contained in the alicyclic diepoxy compound, a content of the isomer is less than 20% in terms of peak area ratio based on the total peak areas of the 3,4,3',4'-diepoxybicyclohexyl compound and the isomer."

While it is believed that the above stated invention of EP2039692A1 is useful and capable of providing the results and articles described therein, it is noted that the purity of such 3,4,3',4'-diepoxybicyclohexyl compound, with respect to epoxy isomers, is limited to only "less that 20%" and as provided in the examples provided by the application to a minimum of 9% (see, PREPARATION EXAMPLE 1 at paragraph [0072]). Therefore it is believed that providing methods of making 3,4,3',4'-diepoxybicyclohexane, as well as other alicyclic diepoxides, that are essentially free of diepoxide isomers of a desired product will be useful.

BRIEF DESCRIPTION OF THE DRAWING

FIG. 1 is a graphical representation of gas chromatograph-mass spectroscopy (GC-MS) analysis of the reaction products resulting from Route A (GC-MS 1) and Route B (GC-MS 2) according to embodiments of the present invention.

DETAILED DESCRIPTION

As used hereinafter, unless otherwise defined, the following abbreviations have the meanings as summarized in the following table.

TABLE 1

| | |
|---|---|
| BCH | 1,1'-bi(cyclohex-3-en-1-yl) |
| ECH | Bi(3,4-epoxycyclohexyl) |
| EpVCH | 1,2 epoxy-4-vinylcyclohexane |
| EpBCH | 3-(3-cyclohexen-1-yl)-7-oxabicyclo[4.1.0]heptane or 4-(3,4-epoxycyclohexyl)-1-cyclohexene |
| VCH | vinylcyclohexene |
| BD | 1,3-butadiene |
| BCH | 4,4'-bi-1-cyclohexene |
| EOHN | 1,2,3,4,4a,5,8,8a-octahydronaphthalene |
| COD | cyclooctadiene |
| THI | tetrahydroindene |
| CTE | coefficient of thermal expansion |
| GC-MS | Gas Chromatograph-Mass Spectrometer. |

Unless otherwise indicated, all numbers, values and/or expressions referring to quantities of ingredients, reaction conditions, ratios, etc., used herein are to be understood as modified in all instances by the term "about" as absent the aforementioned indication, such numbers are approximations reflective of, among other things, the various uncertainties of measurement encountered in obtaining such values. Further, where a numerical range is disclosed herein such range is continuous, and includes every value between the minimum and maximum values of such range. Still further, where a range or ratio refers to integers, every integer between the minimum and maximum values of such range or ratio is included. In addition, where multiple ranges or ratios are provided to describe a feature or characteristic, such ranges or ratios can be combined to further describe such a feature or characteristic.

Embodiments in accordance with the present invention are directed to high purity alicyclic diepoxides (e.g., having purities of ≧95% or ≧98%) and methods for the preparation of such diepoxides. As previously mentioned, EP2039692A1 provides the method for preparing a 3,4,3',4'-diepoxybicyclohexyl compound shown below as Scheme 1

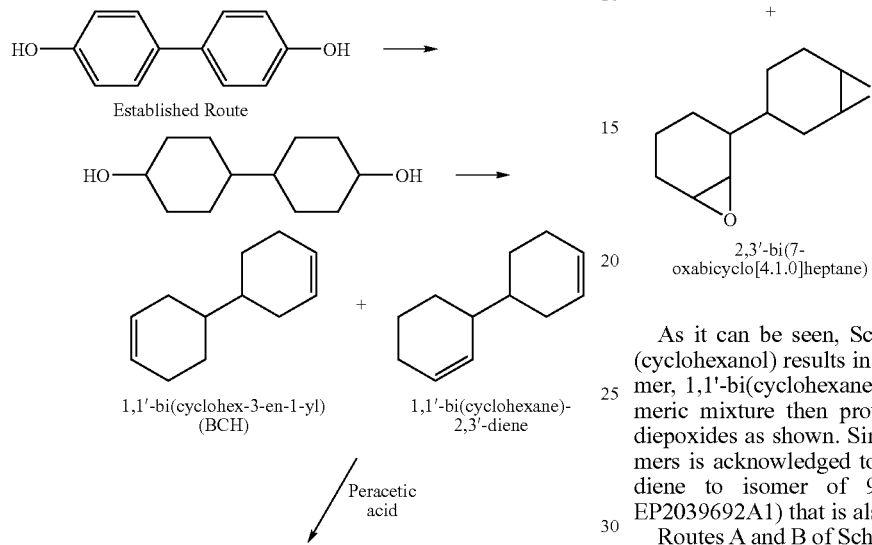

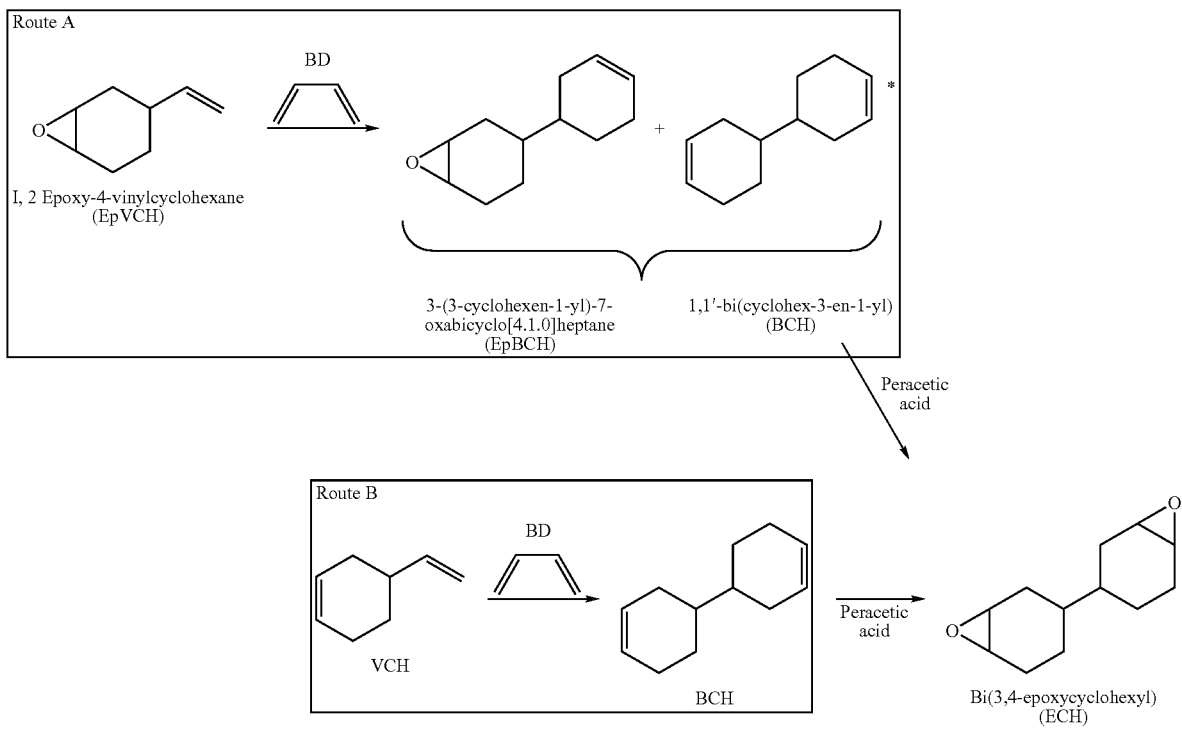

As it can be seen, Scheme 1 the dehydration of 4,4'-bi(cyclohexanol) results in the desired BCH as well as its isomer, 1,1'-bi(cyclohexane)-2,3'-diene. Oxidation of this isomeric mixture then provides an isomeric mixture of the diepoxides as shown. Since the separation of the diene isomers is acknowledged to at best provide a ratio of desired diene to isomer of 91:1 (see, paragraph [0072] of EP2039692A1) that is also the best ratio of diepoxides.

Routes A and B of Scheme 2, below, were thus conceived, studied and developed to avoid the forming of such isomeric dienes and diepoxides.

*Coproduced BCH can be separated from EpBCH prior to epoxidation, if desired

Specifically, embodiments in accordance with the present invention that take advantage of Routes A and B, enable the generation of ECH without the formation of the undesirable diene isomer (1,1'-bi(cyclohexane)-2,3'-diene) intermediate seen in Scheme 1. As a result, the ECH formed is essentially free of any diepoxide isomers such as are present in the methods of EP2039692A1 and other previously known methods. Further, as will be discussed hereinafter, the teachings of Scheme 2 can be used to provide for the development of other embodiments in accordance with the present invention that provide for making alicyclic diepoxides other than ECH.

Still referring to Scheme 2, it was found, upon investigation, that each of Routes A and B could be successfully employed to form the desired ECH in higher purity than afforded by the "Established Route" of Scheme 1. Such investigation showed that each route provided the desired high purity product, as the initial Diels-Alder reaction provided a mixture of by-products that could be readily separated from the ECH diene precursor shown in each route. For example, for the Diels-Alder reaction of 4-vinyl-1-cyclohexene (VCH) with 1,3-butadiene (BD) shown in Route B, by-products such as 2-ethenyl-1,2,3,4,4a,5,8,8a-octahydronaphthalene (EOHN), cyclooctadiene (COD) and several butadiene oligomers are formed as well as the desired ECH precursor 4,4'-bi-1-cyclohexene (BCH).

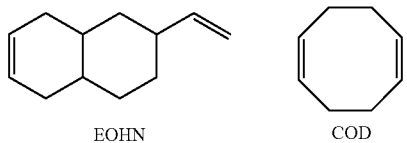

EOHN        COD

Turning now to FIG. 1, it can be seen in GC-MS 2, corresponding to a reaction in accordance with Route B, that only the byproduct EOHN has an elution time (in minutes) close to the desired BCH (13.129 for EOHN v. 14.209 for BCH) however, it has been found that the small relative amount of EOHN observed is readily separable from BCH.

Route A of Scheme 2 was developed based upon the hypothesis, that the presence of the two double bonds in VCH, and particularly the ring double bond, contribute to the formation of EOHN. Therefore, now referring to Route A, it was believed that the reaction of BD with 1,2-epoxy-4-vinylcyclohexane (EpVCH) should form little if any EOHN as a by-product. Referring to FIG. 1, a comparison of GC-MS 1, corresponding to a reaction in accordance with Route A, to GC-MS 2 demonstrates the absence of an EOHN peak, and further, it can be seen that even if EOHN were formed by Route A, the difference in elution times of EpBCH (GC-MS 1) and EOHN (GC-MS 2) would be significantly greater than what is observed for the elution times of BCH and EOHN (e.g., 16.280−13.129=1.080 minutes) observed in GC-MS 2. Still further, as Route A depicts, the principle products are 4-(3,4-epoxycyclohexyl)-1-cyclohexene (EpBCH) and BCH, both of which are readily transformed to the analogous diepoxide, ECH, as shown. Hence even if a significant amount of BCH is formed there is no need to separate it from EpBCH to obtain the desired ECH as an essentially pure product.

To determine if this problem could be overcome, experiments were performed to evaluate the effect of varying: reaction temperature (see, Examples T1-T4); reaction time or duration (see, Experiments D1-D4); and the molar ratio of VCH to BD (see, Experiments M1-M7).

With regard to temperature (see, Examples T1-T4), it was found that: (1) the percentage of BD consumed to produce BCH increases with increasing temperature; (2) the percentage of BD consumed to produce COD increases only slightly with increasing temperature; (3) at 300° C., BD and VCH are polymerized; (4) the selectivity of BCH to COD increases with increasing temperature; and (5) the selectivity of BCH to EOHN decreases with increasing temperature.

Turning now to the effect of varying the duration of the reaction (see, Experiments D1-D4), it was found that: (1) the selectivity of BCH to COD increases with longer reaction time; (2) the selectivity of BCH to EOHN remains essentially unchanged with longer reaction time; and (3) no clear trend for the percentage of BD consumed to produce BCH and COD with longer reaction time.

Referring to the evaluation of molar ratios (see, Examples M1-M7), it was found that: (1) the percentage of BD consumed to produce BCH increases with respect to an increasing VCH/BD molar ratio; (2) the percentage of BD consumed to produce COD remained essentially unchanged with respect to an increasing VCH/BD molar ratio; (3) the selectivity of BCH to COD increases with increases in the VCH/BD molar ratio; and (4) the selectivity of BCH to EOHN isomer remains essentially unchanged with respect to increases in the VCH/BD molar ratio.

Therefore, embodiments in accordance with the present invention provide an optimum yield and purity where such embodiments encompass the preparation of 4,4'-bi-1-cyclohexene (BCH) via Diels-Alder chemistry, where the ratio of starting materials, VCH to 1,3-butadiene (BD) is greater than 1 and as high as 20 to 1. In some embodiments this ratio is 5:1 or greater and in still other embodiments the ratio of starting materials is 10:1 or greater. Appropriate temperatures of the reactions of VCH described above are from 200° C. to 240° C. for some embodiments and from 210° C. to 230° C. for other embodiments. With regard to reaction duration, embodiments in accordance with the present invention are generally from 1 to 10 hours, while other embodiments are from 3 to 6 hours. Advantageously since a major by-product of such embodiments is the VCH starting material, after separation of the desired BCH intermediate, isolated VCH can become feedstock for a subsequent reaction. Alternatively, some embodiments of the present invention encompass semi-batch and/or continuous reactions to take advantage of the formation of VCH.

Advantageously, since BCH can be isolated from the aforementioned reaction method in high purity, for example by a fractional distillation method, the oxidation of the high purity BCH using an appropriate percarboxylic acid method will provide an equally high purity diepoxide. Thus, where BCH is first formed, ECH will be the result of such an appropriate percarboxylic acid oxidation.

It should be noted that since VCH is one of the products of the reaction of BD with itself, embodiments in accordance with the present invention include the in situ formation of VCH accomplished during the formation BCH. Thus, charging a reaction vessel with a desired amount of BD, heating the reaction vessel to a reaction temperature of between 200° C. to 270° C. for a period of from 1 hour to 10 hours and then isolating the desired BCH after cooling encompasses the in situ formation of VCH. Further, contacting the isolated BCH with an appropriate percarboxylic acid under appropriate conditions will result in the formation of the desired ECH.

As previously mentioned, reactions of 1,2-epoxy-4-vinyl-cyclohexane (EpVCH) with 1,3-butadiene (BD) were also studied. Using the data obtained from the VCH-BD study discussed above, the reactions shown in Examples EpVCH 1-4 were performed after evaluating the stability of EpVCH. Such an evaluation was performed in view of an Accelerated Reaction Calorimetry (ARC) Test that reports that EpVCH is unstable at temperatures above 240° C. (See Dow Technical Data Sheet). These evaluations encompassed a GC-MS analysis of an initial sample of EpVCH and then heating that sample to and holding at 210° C. for 1, 2 and 4 hours. At the end of each period of time at 210° C., a portion was withdrawn, allowed to cool and subjected to another GC-MS analysis. Essentially no change in the purity of the EpVCH was observed (initial analysis was 98.0% and after 4 hours 97.2% purity was found).

Referring again to Examples EpVCH 1-4, all of the reactions were run for 3 hours at 230° C. and as indicated in the Summary Table, the ratio of EpVCH to BD was varied from 1:1 to 20:1. As shown in the table and accompanying charts, varying the reactant ratio to increase the amount of EpVCH with respect to BD, significantly reduces the relative amounts of COD and EOHN. Further, the EpBCH formed in these reactions is more readily separated from such by-products (see, FIG. 1 GC-MS 1), and where BCH is formed, there is no need to separate it from the EpBCH as both BCH and EpBCH are readily epoxidized using any appropriate percarboxylic acid, such as percarboxylic acids selected from one or more $C_1$-$C_{12}$ percarboxylic acids having at least one (e.g., 1 or 2) peroxycarboxyl groups (e.g., performic acid, peracetic acid, perpropionic acid, perbutyric acid, perisobutyric acid, meta-chloroperbenzoic acid, and pervaleric acid).

Thus some embodiments in accordance with the present invention encompass the preparation of 4-(3,4-epoxycyclohexyl)-1-cyclohexene (EpBCH) via Diels-Alder chemistry, where the ratio of starting materials, EpVCH to 1,3-butadiene (BD) is greater than 5 and as high as 20 to 1. In some embodiments this ratio is 5:1 or greater and in still other embodiments the ratio of starting materials is 10:1 or greater. Appropriate temperatures of the reactions of EpVCH described above are from 200° C. to 240° C. for some embodiments and from 210° C. to 230° C. for other embodiments. With regard to reaction duration, embodiments in accordance with the present invention are generally from 1 to 10 hours, while other embodiments are from 3 to 6 hours.

As mentioned with regard to the VCH/BD route, the reactions shown in Examples EpVCH 1-4 are followed by the epoxidation of the intermediates EpBCH and BCH formed thereby. Thus these embodiments of the present invention encompass first forming a mixture of EpBCH and BCH where the amount of BCH present can be a little as 0.1% of the amount of EpBCH, and then epoxidizing this mixture with an appropriate percarboxylic acid.

In addition, embodiments in accordance with the present invention provide adding 1,3-butadiene to the reaction mixture in a chilled form due to its low boiling point. Therefore, such embodiments generally employ a reaction pressure of as high as 20 atmospheres when the temperature of the reaction vessel employed is raised. While other lower or higher pressures may be employed, such pressure is, at least in part, a function of the reaction temperature and can be adjusted to maintain an effective amount of BD in the reaction mixture. Such an effective amount of BD being an amount sufficient to react with the VCH or EpVCH present and form BCH or EpBCH.

Further, while only a batch type of reaction is demonstrated herein, alternate reaction schemes such as semi-batch, and continuous schemes will be effective. BD may also be metered into the reactor as a liquid stream or as a gas using a mass flow control device to control the background BD level in the reactor as the reaction is occurring and continuing.

Additionally, in order to obtain good reaction selectivity for product the reactor should be sampled (either incrementally or online) so that the actual reaction composition can be determined. It is further believed that such alternate reaction schemes may provide for improved yield, selectivity and purity of the BCH or EpBCH products. Therefore, embodiments in accordance with the present invention encompass such semi-batch and continuous reaction schemes.

In addition, while it has been found that embodiments of the present invention that provide for the formation of BCH or EpBCH without the use of a reaction solvent result in a higher yield than embodiments that include an appropriate solvent, the use of appropriate solvents is within the scope and spirit of the present invention. Thus some embodiments in accordance with the present invention include the use of solvents with a boiling point sufficiently different than BCH or EpBCH, such as toluene, xylenes, ethylbenzene, methanol, ethanol, propanol, diethyl ether, dipropyl ether, acetone, methylethylketone, pentane, hexane, nonane and decane, so that the reaction product can be readily isolated in high purity. In some cases, the use of an appropriately selected solvent may enable the removal of unwanted reaction by products or residual starting materials.

Still further, while only reactions of 1,3-butadiene with VCH and EpVCH followed by the epoxidation of the desired intermediates have been described in detail, other reactions that make use of the teachings provided herein are within the scope and spirit of the current invention. Such other reactions include, but are not limited to, the reaction schemes provided in Schemes 3-7, which are described in further detail herein below. In addition, it should be noted that while VCH has been represented herein as a starting reactant, it has been shown that VCH is also a product, therefore some embodiments in accordance with the present invention encompass a reaction where BD and cyclopentadiene are provided to a reaction vessel and heated. While such a reaction will form VCH, it will also form a variety of by products that would generally be separated from the desired product. For example, as reported in *Diels-Alder reaction between butadiene and cyclopentadiene. Determination of trimers* by Tsuchida, Shoichi; Hamanaka, Sawako; Ogawa, Masaya. Fac. Eng., Kansai Univ., Suita, Japan, Sekiyu Gakkaishi (1972), 15(3), 189-92, the Diels-Alder reaction of butadiene and cyclopentadiene gave intermediate dimers 4-vinyl-1-cyclohexene, 5-vinylnorbornene, 3a,4,7,7a-tetrahydroindene, and dicyclopentadiene, which reacted further with the monomer dienes to yield 14 trimers, including bicyclohexenyl, binornbornenyl, cyclopenta-, methano-, and vinyloctalin, and fluorene derivatives.

As a result of the discoveries noted above, investigation into other alicyclic diepoxide compounds was carried out and, represented in Scheme 3 below, embodiments in accordance with the present invention that take advantage of endo/exo-vinylnorbornene rearranging under appropriate conditions to form tetrahydroindene (THI) is provided. As the THI formed is readily separated from the unreacted exo-VNB, essentially pure THI can be contacted with a percarboxylic acid to form bicyclononadiene diepoxide.

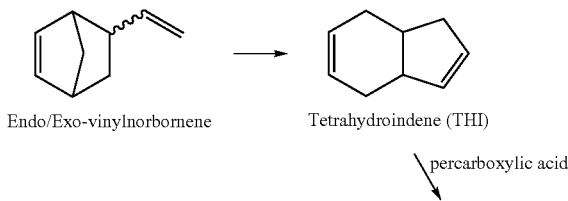

Scheme 3

Endo/Exo-vinylnorbornene        Tetrahydroindene (THI)

percarboxylic acid

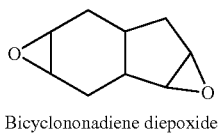

Bicyclononadiene diepoxide

Another embodiment in accordance with the present invention is represented in the following Scheme 4. Specifically, dicyclopentadiene is shown to react via a Diels-Alder reaction with cyclopentadiene to form the tricyclopentadiene structural isomers (I). The tricyclopentadiene structural isomers (I) are then contacted with percarboxylic acid to form the corresponding tricyclopentadiene diepoxide structural isomers (II).

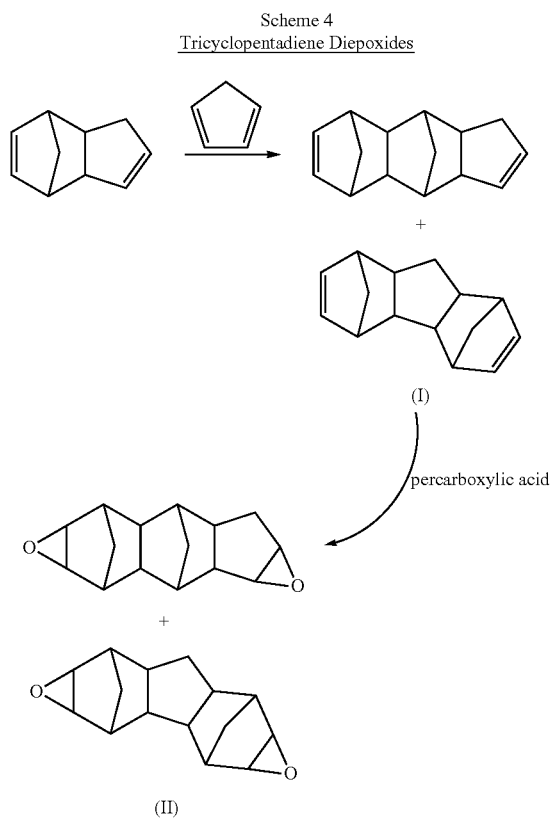

Referring now to the following Scheme 5, yet other embodiments in accordance with the present invention are provided. As shown, 3,4-epoxy-1-butene (III) (also known as 2-ethenyloxirane) reacts via Diels-Alder reaction with cyclopentadiene to form 5-ethylene oxide-2-norbornene (IV). The 5-ethylene oxide-2-norbornene (IV) can then further reacts via Diels-Alder reaction with cyclopentadiene to form the corresponding ethylene oxide functional tetracyclododecene (V), which can be contacted with a percarboxylic acid to form the corresponding oxirane-ethylene oxide functional tetracyclododecene (VI). Alternatively, 5-vinyl-2-norbornene (VII) may be reacted: partially with a percarboxylic acid to form 5-ethylene oxide-2-norbornene (IV); or fully with the percarboxylic acid to form the corresponding 2,3-oxirane-5-ethylene oxide-norbornene (VIII). The 5-ethylene oxide-2-norbornene (IV) may itself be further contacted with a percarboxylic acid to form the corresponding 2,3-oxirane-5-ethylene oxide-norbornene (VIII). The 5-vinyl-2-norbornene (VII) may react via Diels-Alder reaction with cyclopentadiene to form the corresponding vinyl functional tetracyclododecene (IX), which may be contacted with a percarboxylic acid to form the corresponding oxirane-ethylene oxide functional tetracyclododecene (VI).

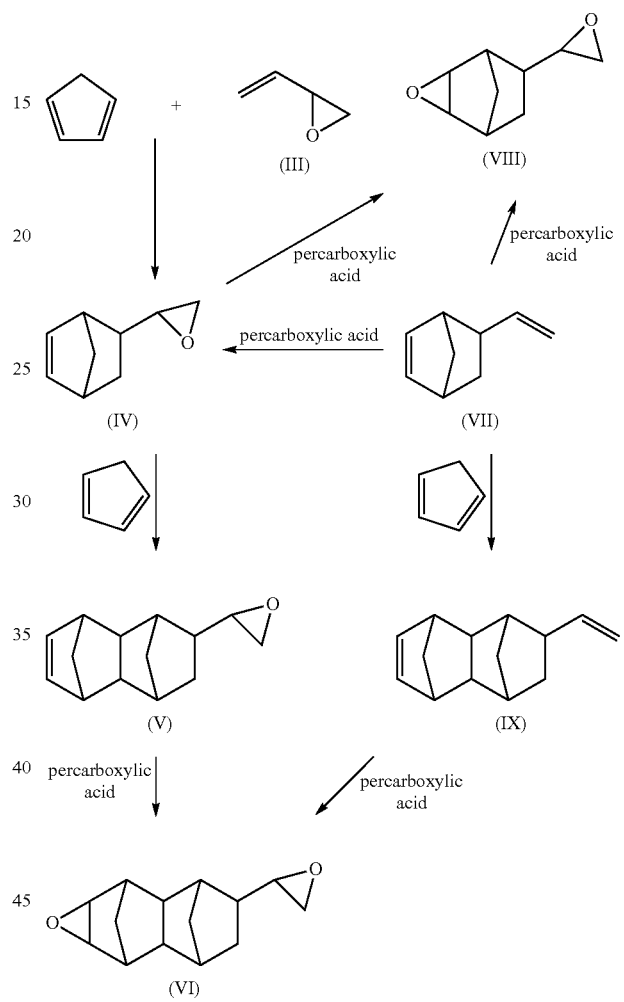

Embodiments in accordance with the present invention also encompasses dienophiles selected from alpha, omega-dienes (α,ω-dienes). With reference to the following Scheme 6, n of alpha, omega-diene (X) is at least 1 (e.g., from 1 to 1000, 1 to 100, 1 to 50 or 1 to 20). As shown, alpha, omega-diene (X) reacts via Diels-Alder reaction with cyclopentadiene to form a 5-vinyl terminated alkyl-2-norbornene (XI). The 5-vinyl terminated alkyl-2-norbornene (XI) may be contacted with a percarboxylic acid to form the corresponding 5-vinyl terminated alkyl-2,3-oxirane-norbornane (XII). The 5-vinyl terminated alkyl-2,3-oxirane-norbornane (XII) may be further reacted with cyclopentadiene to form the 2,3-oxirane-norbornane/norbornene terminated alkyl represented by formula (XIII), which may be contacted with a percarboxylic acid to form the bis(2,3-oxirane-norbornane) terminated alkyl represented by formula (XIV).

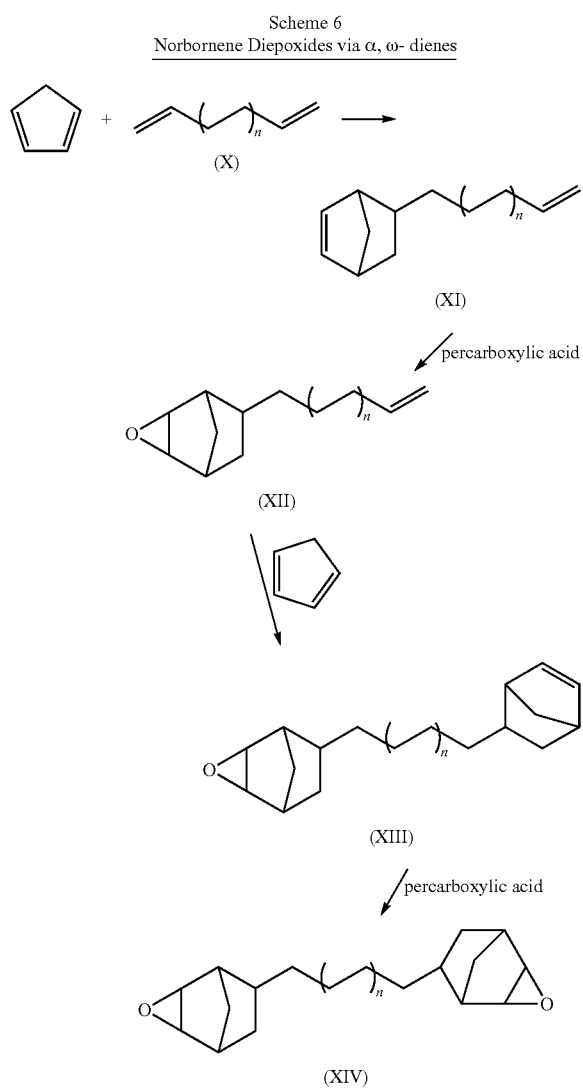

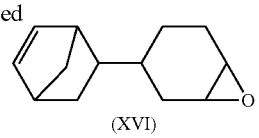

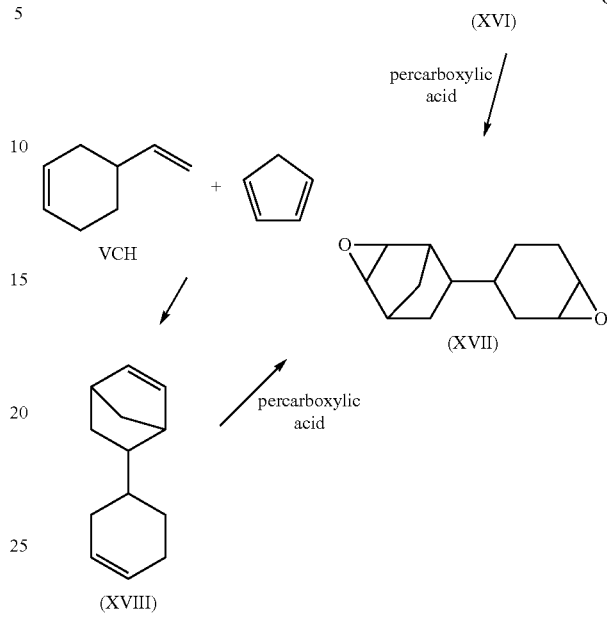

Embodiments in accordance with the present invention also include norbornene cyclohexyl diepoxides and their preparation. With reference to the following Scheme 7, EpVCH is reacted with cyclopentadiene to form 5-EpVCH-2-norbornene (XVI), which may be contacted with a percarboxylic acid to form the corresponding norbornene cyclohexyl diepoxide (XVII). Alternatively, VCH may be reacted with cyclopentadiene to form the corresponding 5-(3-cyclohexene)-2-norbornene (XVIII), which may be contacted with a percarboxylic acid to form the corresponding norbornene cyclohexyl diepoxide (XVII).

Scheme 7
Norbornene Cyclohexyl Diepoxides

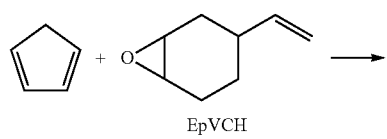

It should be realized, that the alicyclic diepoxide compounds described herein are useful for forming epoxy resin compositions that contain an alicyclic diepoxy compound embodiment according to the present invention (epoxy compound). Where the EP2039692A1 application represents that an alicyclic diepoxide compound having between 9% and 20% of its diepoxide isomer can be cured more quickly (at a higher curing rate) and can give, as a result of curing, cured articles having higher glass transition temperatures and having significantly superior properties such as thermal stability, as compared with equivalents known at the time it was filed, alicyclic diepoxide compound embodiments in accordance with the present invention and made using a method in accordance with the present invention will logically provide cured resins having superior properties to those disclosed in such application. This advantageous result be derived from the alicyclic diepoxide compound embodiments in accordance with the present invention being at least 95% pure and in some embodiments being at least 98% pure (where the percent purity represents the amount of the desired compound obtained using a method embodiment of the invention). Still further, it is believed that the aforementioned result can also be derived from the alicyclic diepoxide compound embodiments in accordance with the present invention being essentially free of alicyclic diepoxide isomers of the desired compound).

It also follows then that the alicyclic diepoxy compounds in accordance with the embodiments of the present invention can be formed into compositions and cured articles in the manner described in paragraphs [0047] through [0064] EP2039692A1 where such paragraphs, and the other paragraphs of such application previously mentioned herein are incorporated into this application by reference.

EXAMPLES

The following examples are provided for illustrative purposes only and are not intended to limit the invention in any way. Unless otherwise indicated, in the following examples and claims, all parts and percentages are by weight, all temperatures are in degrees Celsius, pressure is at or near atmospheric pressure and reaction conditions and materials are anhydrous.

For each of the examples that follow, the amount of either VCH or EpVCH and BD indicated in the specific table for that example was added to a 120 mL autoclave stainless steel reactor base. The autoclave was then assembled and sparged with an inert gas (e.g., argon or nitrogen) for a time sufficient to remove any dissolved oxygen. The vessel was then heated to the specific temperature indicated while stirring and maintained at this temperature for the period of time indicated. Then the reaction mixture was allowed to cool to room temperature and analyzed by GC-MS to determine its composition. The resulting composition found is indicated in one or both of the tables and charts provided below.

Experiments T1-T4 Summary Table
VCH/BD = 1/1
Time = 3 hr

| | Reaction Conditions | | | | | | | Selectivity | |
|---|---|---|---|---|---|---|---|---|---|
| | Temp. | Max. Pressure | Final Pressure | GC-MS Area (%) | | | | COD/ | EOHN/ |
| Exp. # | (° C.) | (MPa) | (MPa) | BCH | EOHN | COD | VCH | BCH | BCH |
| T1 | 180 | 0.7 | 0.5 | 2.1 | 0.1 | 0.9 | 94.8 | 0.43 | 0.05 |
| T2 | 200 | 1.2 | 0.6 | 6.8 | 0.6 | 4.3 | 86.7 | 0.63 | 0.09 |
| T2 | 230 | 1.8 | 0.8 | 11.1 | 1.0 | 3.9 | 83.1 | 0.35 | 0.09 |
| T4 | 270 | 1.6 | Not Measured | 14.3 | 2.3 | 4.3 | 73.8 | 0.30 | 0.16 |

For each of T1-T4 21.64 g of VCH, 10.82 g of BD and 2.6 g of n-nonane (reference) were charged to the reaction vessel Summary Table Experiments D1-D4
VCH/BD = 1/1
Temp = 230° C.

| | reaction conditions | | | | | | | selectivity | | | |
|---|---|---|---|---|---|---|---|---|---|---|---|
| | Time | Max. Pressure | Final Pressure | GC-MS Area (%) | | | | COD/ | EOHN/ | COD/ | VCH/ |
| Exp # | (h) | (MPa) | (MPa) | BCH | EOHN | COD | VCH | BCH | BCH | BCH | BCH |
| D1 | 1 | 1.5 | 1.1 | 8.2 | 0.8 | 3.6 | 84.4 | 0.44 | 0.10 | 0.52 | 8.46 |
| D2 | 3 | 1.8 | 0.8 | 11.1 | 1.0 | 3.9 | 83.1 | 0.35 | 0.09 | 0.41 | 1.27 |
| D3 | 6 | 1.3 | 0.6 | 11.1 | 1.4 | 3.6 | 82.2 | 0.32 | 0.13 | 0.29 | 1.99 |
| D4 | 10 | 1.9 | 0.6 | 11.6 | 1.1 | 3.4 | 83.5 | 0.29 | 0.09 | 0.34 | 2.27 |

For each of D1-D4 21.64 g of VCH, 10.82 g of BD and 2.6 g of n-nonane (reference) were charged to the reaction vessel Experiments M1-M7 Summary Table
nonane = 2.6 g

| | | Experimental conditions | | | | | | | | selectivity | |
|---|---|---|---|---|---|---|---|---|---|---|---|
| | VCH/BD molar ratio | VCH (g) | BD (g) | Max. Pressure (MPa) | Final Pressure (MPa) | GC-MS Area (%) | | | | COD/ BCH | EOHN/ BCH |
| Exp. # | | | | | | BCH | EOHN | COD | VCH | | |
| M1 | 1/1 | 21.6 | 10.8 | 1.3 | 0.6 | 11.1 | 1.4 | 3.6 | 82.2 | 0.32 | 0.13 |
| M2 | 2/1 | 26.0 | 6.5 | couldn't be measured | | 8.8 | 0.4 | 2.3 | 86.3 | 0.26 | 0.05 |
| M3 | 3/1 | 32.5 | 5.4 | 1.0 | 0.6 | 8.4 | 0.7 | 1.26 | 87.6 | 0.15 | 0.08 |
| M4 | 5/1 | 43.3 | 4.3 | 0.8 | 0.6 | 6.5 | 0.6 | 0.9 | 90.0 | 0.13 | 0.09 |
| M5 | 7/1 | 30.3 | 2.2 | 0.8 | 0.6 | 5.9 | 0.6 | 0.8 | 91.7 | 0.14 | 0.10 |
| M6 | 10/1 | 32.5 | 1.6 | 0.6 | 0.6 | 4.5 | 0.5 | 0.5 | 93.3 | 0.11 | 0.11 |
| M7 | 20/1 | 32.5 | 0.8 | 0.7 | 0.5 | 3.1 | 0.3 | 0.3 | 94.4 | 0.10 | 0.10 |

EpVCH Experiments 1-4
Temp = 230° C. for 3 hours

| | starting material | | | | GC-MS Area % | | | | | | Selectivity | | |
| --- | --- | --- | --- | --- | --- | --- | --- | --- | --- | --- | --- | --- | --- |
| | EpVCH | BD | molar ratio | max pressure | | | | | | | EOHN/ (EpBCH + BCH + EOHN) | EpBCH/ (EpBCH + BCH + EOHN) | (EpBCH + BCH)/ (EpBCH + BCH + EOHN) |
| Exp # | (g) | (g) | EpVCH/BD | (Mpa) | EpBCH | BCH | EOHN | COD | EpVCH | VCH | | | |
| EpVCH-1 | 24.8 | 10.8 | 1/1 | 1.2 | 8.97 | 3.17 | 0.23 | 3.60 | 55.11 | 28.37 | 1.86% | 72.50% | 98.14% |
| EpVCH-2 | 49.7 | 4.3 | 5/1 | 0.6 | 7.12 | 0.44 | 0.03 | 0.98 | 80.23 | 11.20 | 0.44% | 93.80% | 99.56% |
| EpVCH-3 | 37.3 | 1.6 | 10/1 | 0.3 | 6.17 | 0.12 | 0.00 | 0.40 | 88.13 | 5.18 | 0.02% | 98.05% | 99.98% |
| EpVCH-4 | 37.3 | 0.8 | 20/1 | 0.2 | 3.51 | 0.02 | 0.00 | 0.13 | 94.50 | 1.84 | 0.00% | 99.35% | 100.00% |

EpVCH Experiments 1-4 represent the reaction of Route A shown in Scheme 2 were the specific amount of EpVCH and BD shown in the table above was added to a reaction vessel, in the manner of the previous examples, to effect the molar ratios shown. A reaction temperature of 230° C. was then provided for 3 hours and the reaction vessel allowed to cool to room temperature. A sample from the reaction vessel was removed and a GC-MS Analysis preformed in the manner of the previous examples. The area for each of the identified products and starting materials was determined and the selectivity of each reaction condition determined. For example, where 1.86% is reported for the selectivity in the first "selectivity" column, such number represents the GC-MS Area of EOHN divided by the sum of the GC-MS areas of EpBCH, BCH and EOHN, multiplied by 100. As it can be seen, where the molar ratio of EpVCH to BCH is increased above 1/1, the selectivity of the reaction increases. While one might comment that the amount of the desired EpBCH formed in any of the four experiments is relatively small, it should be noted that the majority of the EpVCH starting material is recoverable and where the molar ratio of the starting materials exceeds 5/1, the amount of EOHN formed as a side-product is reduced to essentially nil.

Synthesis Example 1

3-Epoxy-5-vinylnorbornane (EVNBA) and
3-epoxy-5-ethylepoxynorbornane

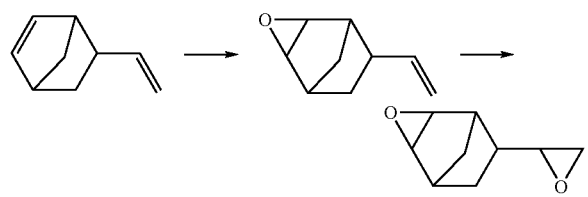

m-Chloroperbenzoic acid (4208 g, 18.77 mol, 1.19 equivalents) was placed in a 72-L flask fitted with mechanical stirrer, thermowell, and addition funnel. 47.5 L dichloromethane was added. The stirred mixture cooled to 4° C. and then was warmed with hot water to 16° C. when all solids dissolved. The mixture was then re-cooled to 5° C., causing some precipitation. An additional 3.5 L dichloromethane was added. The mixture was cooled further to 4° C. before commencing addition of endo-/exo-vinylnorbornene (1900 g, 15.81 mol).

After adding 250 ml vinylnorbornene (VNB), the reaction mixture warmed to 6° C. and cleared. After 600 ml VNB had been added, the mixture began to cloud. The reaction became milky in appearance after 700 ml VNB
had been added. Addition time was 6.5 hours with the temperature ranging from 4° C. to 12° C. GC analysis revealed 28% unreacted VNB, 41% epoxyvinylnorbornene (EVNBA), and 22% diepoxy isomers. KI-starch paper test for peroxide was positive.

After stirring 18 hrs at <4° C., KI-starch paper test for peroxide was negative. GC analysis showed little change in product mix: 28% VNB, 44% EVNBA, and 27% diepoxy. After confirming that additional mCPBA would react preferentially with VNB instead of EVNBA, an additional 877 g of mCPBA (for a total of 5085 g, 22.69 mol) was added in three portions as the solid to the reaction mixture. Additional dichloromethane was added only to rinse in the solids. The addition of solid mCPBA caused a temperature drop to 4° C., which was then followed by a gentle exotherm that caused the temperature to rise to 7° C. GC analysis showed 4% VNB, 63% EVNBA, and 32% diepoxy. KI-starch paper test was positive for peroxide. The reaction mixture was stirred an additional 39 hrs at <12° C. KI-starch paper test was negative for peroxide. GC analysis showed 1.4% VNB, 70% EVNBA, and 26% diepoxy isomers. The reaction mixture was split into two portions. 16.4 liters of saturated sodium bicarbonate solution and ~1 kg of solid sodium bicarbonate was added to each portion. When the solutions did not clear, an additional 1000 g sodium bicarbonate was added to each, followed by 9 L water. The mixtures were stirred for 30 minutes until both had cleared. The phases were separated and the dichloromethane phase was decanted from the undissolved sodium bicarbonate. Each organic phase was washed with 2×16 L brine to pH 7. The undissolved sodium bicarbonate was dissolved with 50 L water, causing separation of ~4 L of dichloromethane. After separating the phases, the aqueous phase was extracted with 2×4 L dichloromethane. The dichloromethane portions were washed with 2×12 L brine to pH 6. All dichloromethane portions were combined and rotary evaporated to give 2654 g of yellow liquid containing some solids. GC analysis showed 1.0% VNB, 75.7% EVNBA, and 20.2% diepoxy isomers. NMR analysis indicated the composition to be 3.1% m-chlorobenzoic acid, 55.5% EVNBA, 14.6% dichloromethane, and 26.7% diepoxy isomers. The crude product was filtered and then vacuum distilled through a 14-inch Vigreux column to yield 1,002 g (>99%)-3-epoxy5-vinylnorbornane (EVNBA) and 109.08 (99.6%) 3-epoxy-5-ethylepoxynorbornane (diepoxies). -

Synthesis Example 2

Synthesis of Norbornene Epoxynorbornane (6-bicyclo[2.2.1]hept-5-en-2-yl-3-oxatricyclo[3.2.1.0$^{2,4}$]octane)

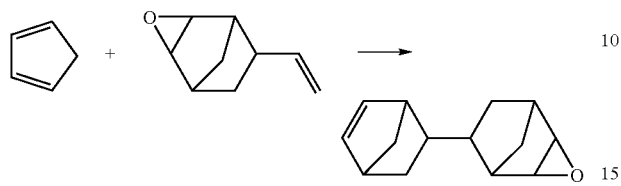

To a 2-liter stainless steel autoclave reactor was charged 0.99 kg (7.26 mol) 3-epoxy-5-vinyl norbornane and 0.06 kg (0.45 mol) dicyclopentadiene. Stirring was started, and the reactor evacuated of air and padded with 5 psig nitrogen. Heating to 180° C. commenced, and upon achieving 180° C., the reactor was held for 4 hours at this temperature. At the end of this time, the reactor was cooled to ambient temperature and discharged. The major identified components of the charge, as measured by GC area, were: 0.6% dicyclopentadiene, 81.6% 3-epoxy-5-vinyl norbornane, 1.3% epoxyethyl-epoxy norbornane, 13.6% norbornenyl epoxy norbornane. A total of four reactions were completed and distilled to produce 0.3 kg norbornenyl epoxy norbornane with assay greater than 96% (GC area).

Synthesis Example 3

Conversion of Norbornene Epoxynorbornane (6-bicyclo[2.2.1]hept-5-en-2-yl-3-oxatricyclo[3.2.1.0$^{2,4}$]octane) to Bis(epoxynorbornane) (6,6'-bi(3-oxatricyclo[3.2.1.0$^{2,4}$]octane))

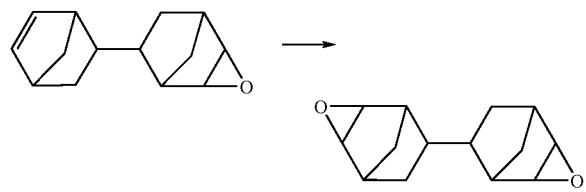

To a three-necked 1 L round bottomed flask equipped with a mechanical stirrer was charged 77 g (312 mmol) of m-CPBA and methylene chloride (600 mL). The mixture was stirred in a water bath maintained at 20° C. until homogeneous. Norbornene epoxynorbornane (52.6 g, 260 mmol) was dissolved in 100 mL methylene chloride. The norbornene solution was added drop wise into the three-necked flask via an addition funnel. Caution was made to make sure the internal temperature never exceeded 25° C. After addition was complete, the white powder suspension was stirred overnight (14 h) at ambient temperature. Saturated NaHCO$_3$ solution was added in 50 mL portions in 4 cycles, with an interval of at least 30 from one cycle to another. After all additions, the mixture was stirred for one hour. The organic phase was separated and washed once more with 250 mL saturated NaHCO$_3$ solution. Combined aqueous phase was washed once with 100 mL methylene chloride. All organic fractions were combined and dried over anhydrous Na$_2$SO$_4$. After filtration, all volatiles were removed under reduced pressure to yield a white powder. Quantitative yield of the desired bis(epoxynorbornane) was obtained (>97% pure by GC). The compound can be further purified by chromatography by loading the re-dissolved bis(epoxynorbornane) onto an alumina column and eluting with ethyl acetate. All faint yellow impurities were removed and GC analysis of final solution suggests the compound is >99% pure. All solvent was removed to yield 50 g diepoxide isomers as a white powder.

Synthesis Example 4

Generation of 3-bicyclo[2.2.1]hept-5-en-2-yl-7-oxabicyclo[4.1.0]heptane (Cyclohexylepoxy norbornene) and Conversion to 6-(7-oxabicyclo[4.1.0]hept-3-yl)-3-oxatricyclo[3.2.1.0$^{2,4}$]octane

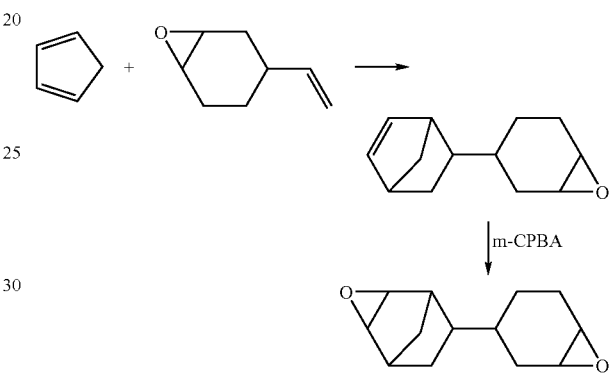

To an 8-liter stainless steel autoclave reactor was charged 5.0 kg (40.3 mol) vinylcyclohexene monoxide-C. Stirring was started, and the reactor evacuated of air and padded with 5 psig nitrogen. Heating to 220° C. commenced, and upon achieving 220° C., the reactor was held for 4.6 hours at this temperature. During this time, a mixture of 0.45 kg (3.6 mol) vinylcyclohexene monoxide-C and 0.48 kg (3.6 mol) dicyclopentadiene were added to the reactor at a constant rate of 3.37 g/min. At the end of the addition, the reactor was cooled to ambient temperature and discharged. The major identified components of the charge, as measured by GC area, were: 0.5% dicyclopentadiene, 73.5% vinylcyclohexene monoxide-C, and 21% cyclohexylepoxy norbornene. A total of two reactions were completed and distilled to produce 2.2 kg cyclohexylepoxy norbornene with assay greater than 96% (GC area). A portion of the product was epoxidized to 6-(7-oxabicyclo[4.1.0]hept-3-yl)-3-oxatricyclo[3.2.1.0$^{2,4}$]octane using m-chloroperbenzoic acid.

Synthesis Example 5

Synthesis of 5-butyl-5-en-1-ylbicyclo[2.2.1]hept-2-ene (Butenyl Norbornene) and of 5,5'-ethyl-1,4-diyl-bis(bicyclo[2.2.1]hept-2-ene) (Ethyl Bisnorbornene—NB-Et-NB)

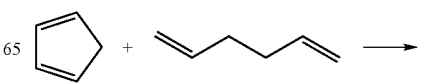

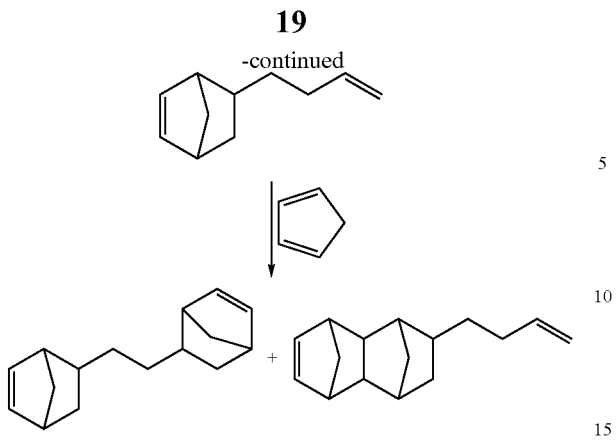

To an 8-liter stainless steel autoclave reactor was charged 2.1 kg (25.6 mol) 1,5-hexadiene. Stirring was started, and the reactor evacuated of air and padded with 5 psig nitrogen. Heating to 200° C. commenced, and upon achieving 200° C., the reactor was held for 3.25 hours at this temperature. During this time, a mixture of 0.05 kg (0.7 mol) 1,5-hexadiene and 0.43 kg (3.3 mol) dicyclopentadiene (DCPD) were added to the reactor at a constant rate of 2.48 g/min. At the end of the addition, the reactor was cooled to ambient temperature and discharged. The major identified components of the charge, as measured by GC area, were: 74.5% 1,5-hexadiene, 1.7% dicyclopentadiene, 19.5% butenyl norbornene, 0.2% cyclopentadiene trimers, 1.4% butenyl tetracyclododecene, and 1.3% ethyl bisnorbornene. A total of five reactions were completed and distilled to produce 1.6 kg butenyl norbornene with assay greater than 99% (GC area), and the portion remaining in the pot consisted primarily of 5.7% cyclopentadiene trimers, 26.3% butenyltetracyclododecene, and 51.2% ethyl bisnorbornene.

Synthesis Example 6

Synthesis of 5-hex-5-en-1-ylbicyclo[2.2.1]hept-2-ene (HexenylNB)

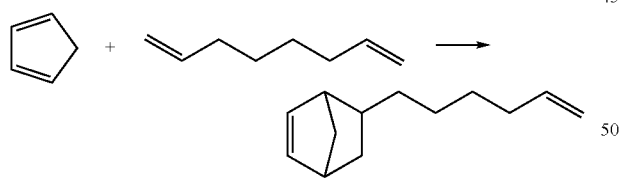

To an 8-liter stainless steel autoclave reactor was charged 2.9 kg (26.3 mol) 1,7-octadiene. Stirring was started, and the reactor evacuated of air and padded with 5 psig nitrogen. Heating to 200° C. commenced, and upon achieving 200° C., the reactor was held for 12 hours at this temperature. During this time, a mixture of 0.26 kg (2.4 mol) 1,7-octadiene and 1.58 kg (12.0 mol) dicyclopentadiene were added to the reactor at a constant rate of 2.56 g/min. At the end of the addition, the reactor was cooled to ambient temperature and discharged. The major identified components of the charge, as measured by GC area, were: 30.4% 1,7-octadiene, 1.7% dicyclopentadiene, 39.2% hexenyl norbornene, 1.0% cyclopentadiene trimers, with the remaining components mostly heavier materials identified as hexenyl tetracyclododecene and butyl bisnorbornene. Purification was accomplished by distillation to produce 2.7 kg hexenyl norbornene with assay greater than 99% (GC area).

Synthesis Example 7

Synthesis of 5,5'-butane-1,4-diylbis(bicyclo[2.2.1]hept-2-ene) (Butyl Bisnorbornene—NB-Bu-NB)

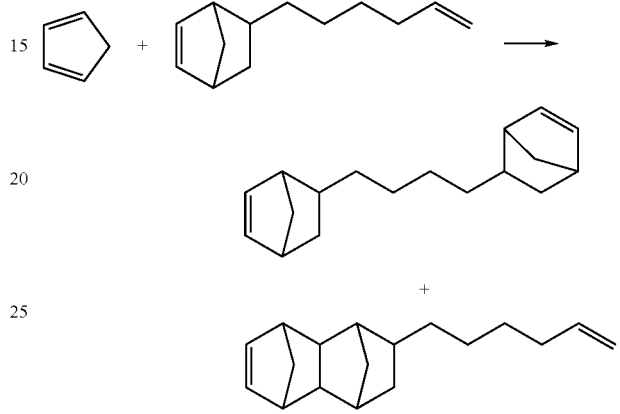

To an 8-liter stainless steel autoclave reactor was charged 3.97 kg (22.5 mol) hexenyl norbornene. Stirring was started, and the reactor evacuated of air and padded with 5 psig nitrogen. Heating to 200° C. commenced, and upon achieving 200° C., the reactor was held for 2.9 hours at this temperature. During this time, a mixture of 0.10 kg (0.6 mol) hexenyl norbornene and 0.38 kg (2.9 mol) dicyclopentadiene were added to the reactor at a constant rate of 2.77 g/min. At the end of the addition, the reactor was cooled to ambient temperature and discharged. The major identified components of the charge, as measured by GC area, were: 1.3% dicyclopentadiene, 73.0% hexenyl norbornene, 0.2% cyclopentadiene trimers, 11.0% hexenyl tetracyclododecene, and 11.2% butyl bisnorbornene. Purification was accomplished by distillation to produce 0.2 kg of 53% hexenyltetracyclododecene and 44.8% butyl bisnorbornene (GC area).

Synthesis Example 8

Conversion of 5,5'-butane-1,4-diylbis(bicyclo[2.2.1]hept-2-ene) (NB-Bu-NB) to 6,6'-butane-1,4-diylbis(3-oxatricyclo[3.2.1.0$^{2,4}$]octane) ((epoxy-NBane)$_2$Bu)

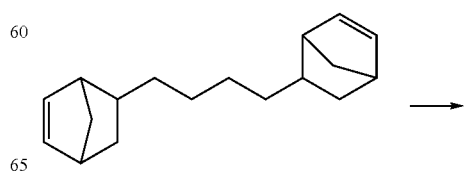

-continued

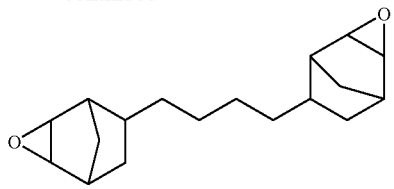

m-Chloroperbenzoic acid (10.24 g, 70-75%, 0.0415 mol, 2.27 equivalents) was placed in a 250 ml flask fitted with mechanical stirrer, thermowell, nitrogen inlet, and addition funnel. 100 ml dichloromethane was added. The stirred mixture cooled to 15° C. as the solids dissolved. The mixture was then cooled to 0° C. 1,4-bis(2-norbornanyl)butane (4.43 g, 0.0183 mol) was added rapidly within one minute. The temperature rose to 13° C., as precipitation of chlorobenzoic acid occurred. The reaction was stirred at about 0-3° C. for 2 hours. GC analysis showed 89.9% epoxy products with 1.1% unreacted starting material. The mixture was allowed to warm to room temperature over 1.5 hrs. GC analysis showed no further reaction progress. The solids were filtered and washed with dichloromethane. The combined dichloromethane solutions were washed with 3×50 ml saturated aqueous sodium bicarbonate to pH 9 and then washed two times with a mixture of 30 ml 10% aqueous sodium bisulfite and 30 ml saturated aqueous sodium bicarbonate solution. The dichloromethane solutions still gave a positive KI/starch paper test for peroxide. The dichloromethane solutions were then washed with 100 ml 10% aqueous sodium bisulfite to give a negative KI/starch paper test. The dichloromethane solutions were washed with 50 ml saturated aqueous sodium bicarbonate, washed with 100 ml brine to pH 8, and then dried over sodium sulfate. The solution was filtered and rotary evaporated to 5.1 g oil. GC analysis found a broad signal indicating 87.5% diepoxy compound. The oil crystallized overnight. The solid was taken up in pentane and filtered to give white solid. GC analysis showed two main components of totalling 89.5% diepoxy compounds. Two subsequent precipitants from the pentane washes showed 87.7-88.4% total isomer content on GC analysis. Total product collected was 2.52 g. This was treated with ~10 ml pentane, mixed thoroughly, and filtered. The solid was washed with 5 ml pentane. GC analysis showed a double-peaked signal indicating 91% total diepoxy compound. Additional material precipitated from the pentane filtrate for which GC analysis found two isomer signals of 55.2% and 41.7% to give 96.9% total isomer. This was combined with previously collected solid to give 1.77 g (35% yield).

Synthesis Example 9

Conversion of Norbornene Epoxynorbornane to Bis(epoxynorbornane)

To a three-necked 1 L round flask equipped with a mechanical stirrer was charged 77 g (312 mmol) of mCPBA and methylene chloride (600 mL). The mixture was stirred in a water bath maintained at 20° C. until homogeneous. Norbornene epoxynorbornane (52.6 g, 260 mmol) was dissolved in 100 mL methylene chloride. The norbornene solution was added dropwise into the three-necked flask via a dropper funnel. Caution was made to make sure the internal temperature never exceeded 25° C.; addition was halted and ice was added to cool the reaction back to 20° C. when the monitored temperature reached 25° C. After all additions, the white powder suspension was stirred overnight (14 h). Saturated NaHCO$_3$ solution was added in 50 mL portions in 4 cycles, with an interval of at least 30 from one cycle to another. After all additions, the mixture was stirred for one hour. The organic phase was separated and washed once more with 250 mL saturated NaHCO$_3$ solution. Combined aqueous phase was washed once with 100 mL methylene chloride. All organic fractions were combined and dried over anhydrous Na$_2$SO$_4$. After filtration, all volatiles were removed under reduced pressure to yield a white powder. Quantitative yield of the desired bis(epoxynorbornane) was obtained (>97% pure by GC). The compound can be further purified by chromatography by loading the re-dissolved bis(epoxynorbornane) onto an alumina column and eluting with ethyl acetate. All faint yellow impurities will be removed, GC of final solution suggests the compound is >99% pure. All solvent was removed to get at least 50 g white powder of the diepoxide isomers.

By now it should be realized that embodiments in accordance with the present invention have been disclosed that provide for the formation of high-purity alicyclic diepoxides. Such embodiments make use of reactions that can form a high purity precursor that is readily epoxidized using an appropriate organic peracid. Further, unlike the Established Route shown in Scheme 1, embodiments in accordance with the present invention do not form isomeric variations of the diepoxides, such as 1,1'-bi(cyclohexane)-2,3'-diene, that are extremely difficult to separate from the desired product. As a result, the embodiments of the present invention provide useful alicyclic diepoxides that are essentially free of isomeric by-products or residues.

The invention claimed is:
1. A method for forming an alicyclic diepoxide comprising:
    charging a reaction vessel with a first amount of an appropriate dienophile and a second amount of an appropriate diene to form a reaction mixture, where the molar ratio of the first amount to the second amount is greater than 5:1 and less than or equal to 20:1;
    heating the reaction mixture to a reaction temperature from 200° C. to 270° C.;
    maintaining the reaction mixture at the reaction temperature for from 1 hour to 10 hours;
    allowing the reaction mixture to cool to room temperature and recovering a desired alicyclic diepoxide precursor; and
    epoxidizing the desired alicyclic diepoxide precursor,
    where said appropriate dienophile is selected from at least one of,
    1,1'-bi(cyclohex-2-en-yl),
    1,1'-bi(cyclohexene)-2,3'-diene,
    1,2-epoxy-4-vinylcyclohexane,
    4,-(3,4-epoxycyclohexyl)-1-cyclohexene,
    vinylcyclohexene,
    1,2,3,4,4a,5,8, 8a-octahydronaphthalene,
    cyclooctadiene,
    dicyclopentadiene,
    3,4-epoxy-1-butene,
    5-ethylene oxide-2-norbornene,
    ethylene oxide functional tetracyclododecene represented by the following formula (V)

(V)

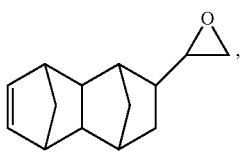

vinyl functional tetracyclododecene represented by the following formula (IX)

(IX)

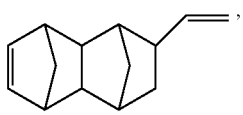

alpha, omega dienes represented by the following formula (X)

(X)

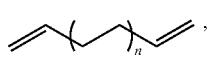

where n is from 1 to 1000,
5-vinyl terminated alkyl-2,3-oirane-norbornene represented by the following formula (XII)

(XII)

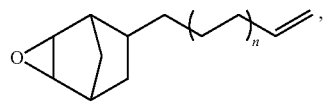

where n is from 1 to 1000,
2,3-oxirane-norbornane/norbornene terminated alkyl represented by the following formula (XIII)

(XIII)

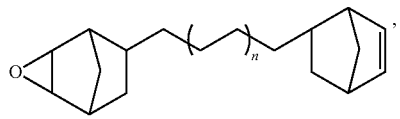

where n is from 1 to 1000,
5-(1,2-epoxy cyclohexane)-2-norbornene represented by the following formula (XVI), (XVI)

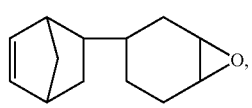

5-(3-cyclohexanene)-2-norbornene represented by the following formula (XVIII), (XVIII)

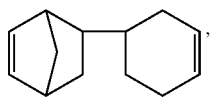

a tricyclopentadiene structural isomer represented by the following formula (IA), (IA)

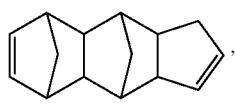

and
a tricyclopentadiene structural isomer represented by the following formula (IB)

(IB)

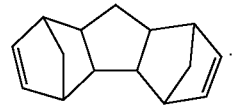

2. The method of claim 1, where charging a reaction vessel with a first amount of an appropriate dienophile comprises charging the reaction vessel with vinylcyclohexene.

3. The method of claim 1, where charging a reaction vessel with a first amount of an appropriate dienophile comprises charging the reaction vessel with 1,2-epoxy-4-vinylcyclohexane.

4. The method of claim 2 or 3, where charging a reaction vessel with a second amount of an appropriate diene comprises charging the reaction vessel with 1,3-butadiene.

5. The method of claim 2, where charging a reaction vessel with a second amount of an appropriate diene comprises charging the reaction vessel with 1,3-butadiene and where the ratio of the first amount to the second amount is greater than or equal to 10:1 and less than or equal to 20:1.

6. The method of any of claims 1-3 and 5 where heating the reaction mixture to a temperature comprises heating the reaction mixture to a temperature from 220° C. to 250° C.

7. A method for forming an alicyclic diepoxide represented by the following formula:

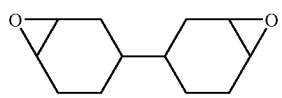 [SMILES: C1CC2OC2CC1C1CCC2OC2C1]

comprising:
charging a reaction vessel with an amount of 1,3-butadiene;
heating the reaction mixture to a reaction temperature from 200° C. to 270° C.;
maintaining the reaction mixture at the reaction temperature for from 1 hour to 10 hours;
allowing the reaction mixture to cool to room temperature and recovering a desired alicyclic diepoxide precursor; and
epoxidizing the desired alicyclic diepoxide precursor.

* * * * *

UNITED STATES PATENT AND TRADEMARK OFFICE
CERTIFICATE OF CORRECTION

PATENT NO. : 8,389,752 B2
APPLICATION NO. : 12/577845
DATED : March 5, 2013
INVENTOR(S) : Andrew Bell et al.

It is certified that error appears in the above-identified patent and that said Letters Patent is hereby corrected as shown below:

Title Page of the Patent, Column 1, Item (73) Assignee, Line 1, "Peomerus" should read
-- Promerus --

Title Page of the Patent, Column 2, OTHER PUBLICATIONS, Line 2, delete "Diels-Aider" and insert
-- Diels-Alder --

Title Page of the Patent, Column 2, OTHER PUBLICATIONS, Line 3, delete "Sewako" and insert
-- Sawako --

Title Page of the Patent, Column 2, OTHER PUBLICATIONS, Lines 4-5, delete "Gakkaish" and
insert -- Gakkaishi --

Title Page of the Patent, Column 2, OTHER PUBLICATIONS, Line 9, delete "Verlang Chermie" and
insert -- Verlag Chemie --

In the Claims:

Column 22, Line 59, Claim 1, delete "8, 8a" and insert -- 8,8a --

Column 23, Line 42, Claim 1, delete "norbomene" and insert -- norbornene --

Column 23, Line 31, Claim 1, delete "oirane" and insert -- oxirane --

Column 23, Line 64, Claim 1, delete "cyclohexanene" and insert -- cyclohexene --

Signed and Sealed this
Twenty-first Day of May, 2013

Teresa Stanek Rea
*Acting Director of the United States Patent and Trademark Office*